United States Patent [19]

Steiner et al.

[11] Patent Number: 6,040,479
[45] Date of Patent: Mar. 21, 2000

[54] RACEMIC SEPARATION OF KETAMINE

[75] Inventors: Klaus Steiner, Emmendingen; Stefan Gangkofner, Lahr, both of Germany; Jean-Marie Grunenwald, Kertzfeld-Benfeld, France

[73] Assignees: Goedecke Aktiengesellschaft, Berlin; Cu Chemie Uetikon GmbH, Lahr, both of Germany

[21] Appl. No.: 09/180,530

[22] PCT Filed: May 7, 1997

[86] PCT No.: PCT/EP97/02360

§ 371 Date: Nov. 10, 1998

§ 102(e) Date: Nov. 10, 1998

[87] PCT Pub. No.: WO97/43244

PCT Pub. Date: Nov. 20, 1997

[30] Foreign Application Priority Data

May 15, 1996 [DE] Germany .......................... 196 19 665

[51] Int. Cl.$^7$ ...................................................... C07B 57/00
[52] U.S. Cl. ............................................. 564/304; 564/307
[58] Field of Search ...................................... 564/304, 307

[56] References Cited

FOREIGN PATENT DOCUMENTS 2062620  12/1969  Germany .

*Primary Examiner*—Samuel Barts
*Attorney, Agent, or Firm*—Elizabeth M. Anderson

[57] ABSTRACT

The present invention is concerned with an improved process for the resolution of racemic 2-(o-chlorophenyl)-2-methylaminocyclohexanone (ketamine).

12 Claims, No Drawings

RACEMIC SEPARATION OF KETAMINE

This application is a 371 of PCT/EP97/02360 filed May 7, 1997.

DESCRIPTION

The present invention concerns an improved process for the resolution of racemic 2-(o-chlorophenyl)-2-methylaminocyclohexanone (ketamine).

Pharmacological investigations show clear qualitative and quantitative differences between the R- and S-ketamine enantiomers. Not only preclinically but also in a clinical study, S-ketamine always behaves better than the antipode or the racemate. From these points of view, the exclusive therapeutic use of the enantiomer is to be preferred, as to the resolution of the racemate. Therefore, in the following, the S-enantomer is always meant which as salt is present in the S-(+)-configuration and as pure base in the S-(−)-configuration.

From German published specification DE-A-2 062 620 is known a process for the resolution of racemic 2-(o-chlorophenyl)-2-methylaminocyclohexanone in which racemic 2-(o-chlorophenyl)-2-methylaminocyclohexanone is reacted with the use of an enantiomeric form of tartaric acid in a solvent mixture of water and acetone, the tartaric acid salt formed is isolated by filtration and subsequent double recrystallisation with acetonitrile, whereupon one isomer is liberated from the tartaric acid salt by reaction with alkali. However, the process suffers from poor yields, the use of toxic solvents, impure products and the necessity of having to carry out many process steps.

Therefore, it was the task of the present invention to provide an improved process for the resolution of racemic 2-(o-chlorophenyl)-2-methylaminocyclohexanone in which the above difficulties do not occur.

Consequently, the subject of the present invention is a process for the resolution of racemic 2-(o-chlorophenyl)-2-methylaminocyclohexanone of the formula:

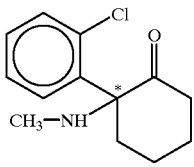

wherein * signifies an asymmetrical carbon atom, which comprises the following steps:

1) reaction of racemic 2-(o-chlorophenyl)-2-methylaminocyclohexanone with an enantiomeric form of tartaric acid, 2) isolation of the formed tartaric acid salt of 2-(o-chlorophenyl)-2-methylaminocyclohexanone and 3) reaction of the isolated tartaric acid salt of 2-(o-chlorophenyl)-2-methylaminocyclohexanone with alkali, whereby an isomer of 2-(o-chlorophenyl)-2-methylaminocyclohexanone can be isolated, whereby steps 1 and 2 are carried out in water or a mixture of water and an alcohol and/or ketone, ether or ester.

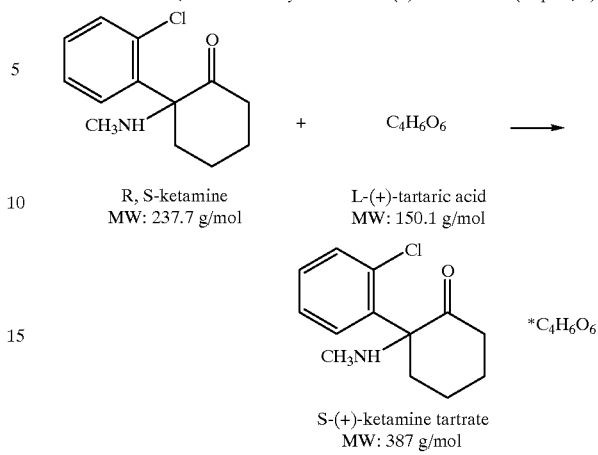

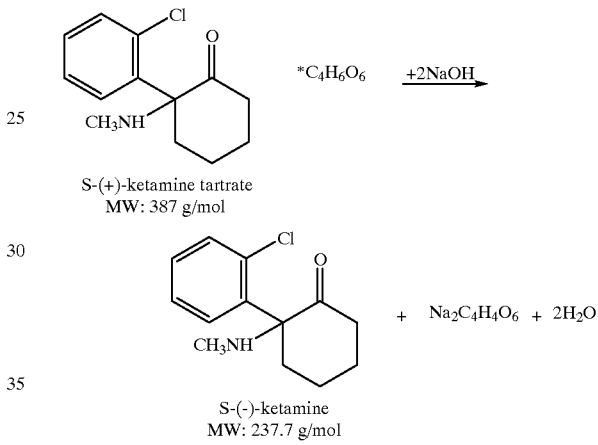

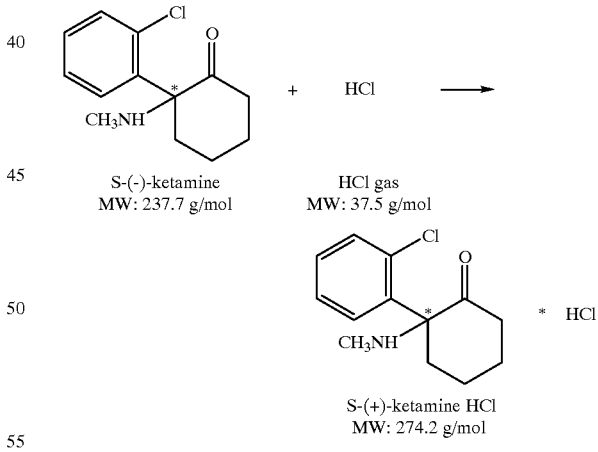

In the scope of the process according to the present invention, racemic 2-(o-chlorophenyl)-2-methylaminocyclohexanone is reacted in a first step with an enantiorneric form of tartaric acid with the formation of a tartaric acid salt of 2-(o-chlorophenyl)-2-methylaminocyclohexanone. As solvent in this reaction, there are used water or a mixture of water and an organic solvent selected from the group consisting of straight-chained or branched $C_1$–$C_6$-alcohols and/or ketones, esters or ethers, preferably isopropanol and/or acetone. Water or a mixture of water and isopropanol or a mixture of water or acetone is preferably used. In the case of using a mixture of water and isopropanol, the ratio of water:isopropanol is preferably 1.5:1. In the case of using a mixture of water and acetone, the ratio of water:acetone is preferably 1:0.33–5.0 and especially 1:3. Other organic solvents which can also be considered include, for example, methanol, ethanol, n-propanol, butanol, t-butanol, pentanol, hexanol, methyl ethyl ketone, dimethyl ketone, propyl methyl ketone and/or ethyl acetate.

In a second step, the formed tartaric acid salt of 2-(o-chlorophenyl)-2-methylaminocyclohexanone is isolated, this preferably taking place by filtration. In the case of using a mixture of water and acetone in a ratio of 1:10–20, the tartaric acid salt formed is, preferably after an isolation for the further enrichment of an enriched tartrate of an isomer of 2-(o-chlorophenyl)-2-methylaminocyclohexanone from the solvent mixture used in step, recrystallised from water and acetone. In the case of the use of water or of a mixture of water and isopropanol or of a mixture of water and acetone in a ratio of 1:0.33–5.0 as solvent, a recrystallisation of the isolated tartaric acid salt of 2-(o-chlorophenyl)-2-methylaminocyclohexanone can be omitted.

In the third step, the tartrate of 2-(o-chloro-phenyl)-2-methylaminocyclohexanone obtained in step 2 is reacted with alkali, a crystalline product thereby being obtained, this being an isomer-pure 2-(o-chloro-phenyl)-2-methylaminocyclohexanone. This can be obtained, for example, by filtration.

Subsequently, the isomer-pure ketamine can be converted with hydrochloric acid into the corresponding hydrochloride.

In the following, the present invention is further illustrated on the basis of examples. It is to be understood that the examples in no way limit the scope of the present invention.

EXAMPLE 1

50 g (0.21 mol) R,S-ketamine are dissolved in 613 ml of acetone at the boiling point and subsequently mixed with 31.5 g (0.21 mol) L-(+)-tartaric acid. In order to obtain a clear solution, 40 ml of water are added thereto at the boiling point and subsequently the clear solution is filtered off while still hot. After the addition of seed crystals obtained in a small preliminary experiment, the whole is allowed to cool to ambient temperature while stirring. After standing overnight, the crystals formed are filtered off with suction and dried in a circulating air drying cabinet (first at ambient temperature and then at 50–60° C.).

Yield (tartrate): 64.8 g
m.p.: 161° C.
$[\alpha]_D$: +26.1° (c=2/H$_2$O)

Thereafter, the crystallisate is recrystallised in a mixture of 1226 ml acetone and 90 ml water. After cooling to ambient temperature and subsequently stirring for 4 hours, the crystals are filtered off with suction and dried in a circulating air drying cabinet (first at ambient temperature and then at 50–60° C). There are obtained 38.8 g of tartrate (95.29% of theory).
m.p.: 175.3° C.
$[\alpha]_D$: +68.9° (c=2/H$_2$O)

The base is liberated by taking up 38.8 g of tartrate in 420 ml of aqueous sodium hydroxide solution and stirring with 540 ml of diethyl ether. The ethereal phase is first washed with water and subsequently with a saturated solution of sodium chloride. The organic phase is dried over anhydrous sodium sulphate. After filtering, the solution is evaporated to dryness on a rotary evaporator, a crystalline, colourless product remaining behind.

Yield (crude base): 21.5 g=86.0% of theory
m.p.: 118.9° C. (literature: 120–122° C.)
$[\alpha]_D$: −55.8° (c=2/EtOH) (literature: $[\alpha]_D$: −56.35° ).

In order possibly to achieve a further purification, the base can be recrystallised from cyclohexane. For this purpose, 10.75 g of the crude base are dissolved in 43 ml cyclohexane at the boiling point. While stirring, the clear solution is slowly cooled to about 10° C. and then stirred at this temperature for about 1 hour. The crystallisate which precipitates out is filtered off with suction and dried to constant weight.

Yield (base): 10.3 g=82.4% of theory
m.p.: 120° C. (literature: 120–122° C.)
$[\alpha]_D$: −56.8° (c=2/EtOH) (literature: $[\alpha]_D$: −56.35° )

EXAMPLE 2

125 ml of water are taken and subsequently 31.5 g (0.21 mol) L-(+)-tartaric acid and 50 g (0.21 mol) R,S-ketamine added thereto. While stirring, this mixture is warmed to 50–60° C. until a clear solution results. After cooling to ambient temperature while stirring and subsequently stirring overnight, the crystals formed are filtered off with suction. Subsequently, the crystallisate is first washed with water (1–6° C.) and subsequently washed twice with, in each case, 20 ml of acetone. Drying in a circulating air drying cabinet (first at ambient temperature and then at 50–60° C.) gives 31.79 g of tartrate (78.23%) of theory).

EXAMPLE 3

150 ml of water are taken and subsequently mixed with 39.8 g (0.27 mol) L-(+)-tartaric acid and 50 g (0.21 mol) R,S-ketamine. While stirring, this mixture is warmed to 50–60° C. until a clear solution results.

After cooling to ambient temperature while stirring and subsequently stirring overnight, the crystals formed are filtered off with suction. Subsequently, the crystallisate is successively washed with 8 ml of water (1–6° C.) and thereafter twice with, in each case, 20 ml acetone.

Drying in a circulating air drying cabinet (first at ambient temperature and then at 50–60° C.) gives 32.58 g of tartrate (80.02% of theory).

EXAMPLE 4

150 ml of water and 50 ml isopropanol are taken. After the addition of 39.8 g (0.21 mol) L-(+)-tartaric acid and 50 g (0.21 mol) R,S-ketamine, the mixture is heated to reflux temperature while stirring until a solution results (possibly add water until all is dissolved).

Subsequently, while stirring, the solution is allowed to cool to ambient temperature and stirred overnight. The crystals are filtered off with suction and subsequently washed with a 1:2 mixture of 20 ml of water/isopropanol and dried in a circulating air drying cabinet (first at ambient temperature and then at 50–60° C.). There are obtained 24.45 g of tartrate (62.63% of theory).

EXAMPLE 5

50 g (0.21 mol) R,S-ketamine are dissolved at the boiling point in 300 ml acetone and subsequently mixed with 31.5 g (0.21 mol) L-(+)-tartaric acid and 100 ml of water. The whole is allowed to cool while stirring and possibly seeded.

After standing overnight, the crystals formed are filtered off with suction, then washed twice with, in each case, 20 ml acetone and dried in a circulating air drying cabinet (first at ambient temperature and then at 50–60° C.). There are obtained 30.30 g of tartrate (74.57% of theory).

EXAMPLE 6

75 ml of water and 50 ml isopropanol are taken and subsequently 39.8 g (0.27 mol) L-(+)-tartaric acid added thereto. While stirring, the mixture is heated to reflux temperature until a clear solution results. After cooling to ambient temperature while stirring and subsequently stirring overnight, the crystals formed are filtered off with suction. Subsequently, the crystallisate is washed with a 1:2 mixture of 20 ml water/isopropanol. After drying in a circulating air drying cabinet (first at ambient temperature and then at 50–60° C.), there are obtained 34.84 g of tartrate (85.74% of theory).

EXAMPLE 7

20 g of the S-(+)-tartrate obtained in Example 4 are dissolved in 100 ml of water at 30–40° C. With about 7 ml of 50% sodium hydroxide solution, an S-(−)-ketamine base is precipitated out up to about pH 13. It is filtered off with suction and washed neutral with water to pH 7–8. Subsequently, it is dried for about 24 hours at 50° C. in a circulating air drying cabinet. There are obtained 11.93 g S-(−)-ketamine (97.79% of theory).

EXAMPLE 8

5 g of the S-(−)-ketamine obtained in Example 7 are dissolved in 50 ml isopropanol at about 50° C. and possibly filtered off with suction over kieselguhr. Subsequently, gaseous hydrogen chloride is passed in at 50–60° C. until a pH value of 0–1 is reached. The reaction mixture is allowed to cool to ambient temperature, filtered off with suction and washed with about 5 ml isopropanol. The moist product is dried overnight at about 50° C. in a circulating air drying cabinet. There are obtained 5.09 g S-(+)-ketamine hydrochloride (88.06% of theory).

We claim:

1. Process for the resolution of racemic 2-(o-chlorophenyl)-2-methylaminocyclohexanone of the formula:

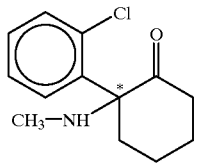

wherein * is an asymmetric carbon atom, which comprises the following steps:

1) reaction of racemic 2-(o-chlorophenyl)-2-methylaminocyclohexanone with an enantiomeric form of tartaric acid,
2) isolation of the formed tartaric acid salt of 2-(o-chlorophenyl)-2-methylaminocyclohexanone and
3) reaction of the isolated tartaric acid salt of 2-(o-chlorophenyl)-2-methylaminocyclohexanone with an alkali, whereby an isomer of 2-(o-chlorophenyl)-2-methylaminocyclohexanone can be isolated, wherein steps 1 and 2 are carried out in water or in a mixture of water and an alcohol and/or ketone, ether or ester.

2. Process according to claim 1, wherein the solvent in step 1 and step 2 is water or a mixture of water and isopropanol and/or acetone.

3. Process according to claim 1, wherein the solvent in step 1 and step 2 is water.

4. Process according to claim 1, wherein the solvent in step 1 and step 2 is a mixture of water and isopropanol.

5. Process according to claim 4, wherein the ratio of water:isopropanol is 1.5:1.

6. Process according to any of the preceding claims, wherein an aqueous solution of sodium hydroxide is used as alkali.

7. Process according to claim 1, wherein the free isomer obtained of 2-(o-chlorophenyl)-2-methylaminocyclohexanone is subsequently converted into the hydrochloride salt of the isomer in question by reaction with hydrochloric acid.

8. Process according to claim 1, wherein the ratio of water:acetone is in the range of 1:0.3–5.0.

9. Process according to claim 1, wherein the ratio of water:acetone is in the range of 1:3.

10. Process according to claim 1, wherein the ratio of water:acetone is in the range of 1:10–20.

11. Process according to claim 1, wherein the tartaric acid salt of 2-(o-chlorophenyl)-2-methylaminocyclohexanone isolated in step 2 is reacted directly in step 3 without subsequent recrystallisation.

12. Process according to claim 9, wherein the tartaric acid salt of 2-(o-chlorophenyl)-2-methylaminocyclohexanone isolated in step 2 is recrystallised before carrying out step 3.

* * * * *